United States Patent [19]

Fujimoto et al.

[11] 4,238,491

[45] Dec. 9, 1980

[54] METHOD FOR TREATING HYPERTENSION WITH METHYLRESERPATE

[75] Inventors: Yasuo Fujimoto, Tokyo; Hiroshi Katagihara, Misato, both of Japan

[73] Assignee: Nippon Chemiphar Co., Ltd., Tokyo, Japan

[21] Appl. No.: 904,290

[22] Filed: May 9, 1978

[30] Foreign Application Priority Data

May 10, 1977 [JP] Japan .................................. 52-53599

[51] Int. Cl.³ .......................................... A61K 31/475
[52] U.S. Cl. .................................................. 424/262
[58] Field of Search ........................................ 424/262

[56] References Cited
PUBLICATIONS

Creveling et al.: J. Med. Chem., 11 596 (1968).
Dhar et al.: J. Sci. Ind. Res., 140, 179 (1955).

*Primary Examiner*—Leonard Schenkman
*Attorney, Agent, or Firm*—Armstrong, Nikaido, Marmelstein & Kubovcik

[57] ABSTRACT

Hypertension in human is treated by orally administering an effective amount of methylreserpate with little or no undesirable side effect such as central nervous system depression. Methylreserpate can be prepared from Reserpine, a Rauwolfia alkaloid.

1 Claim, 18 Drawing Figures

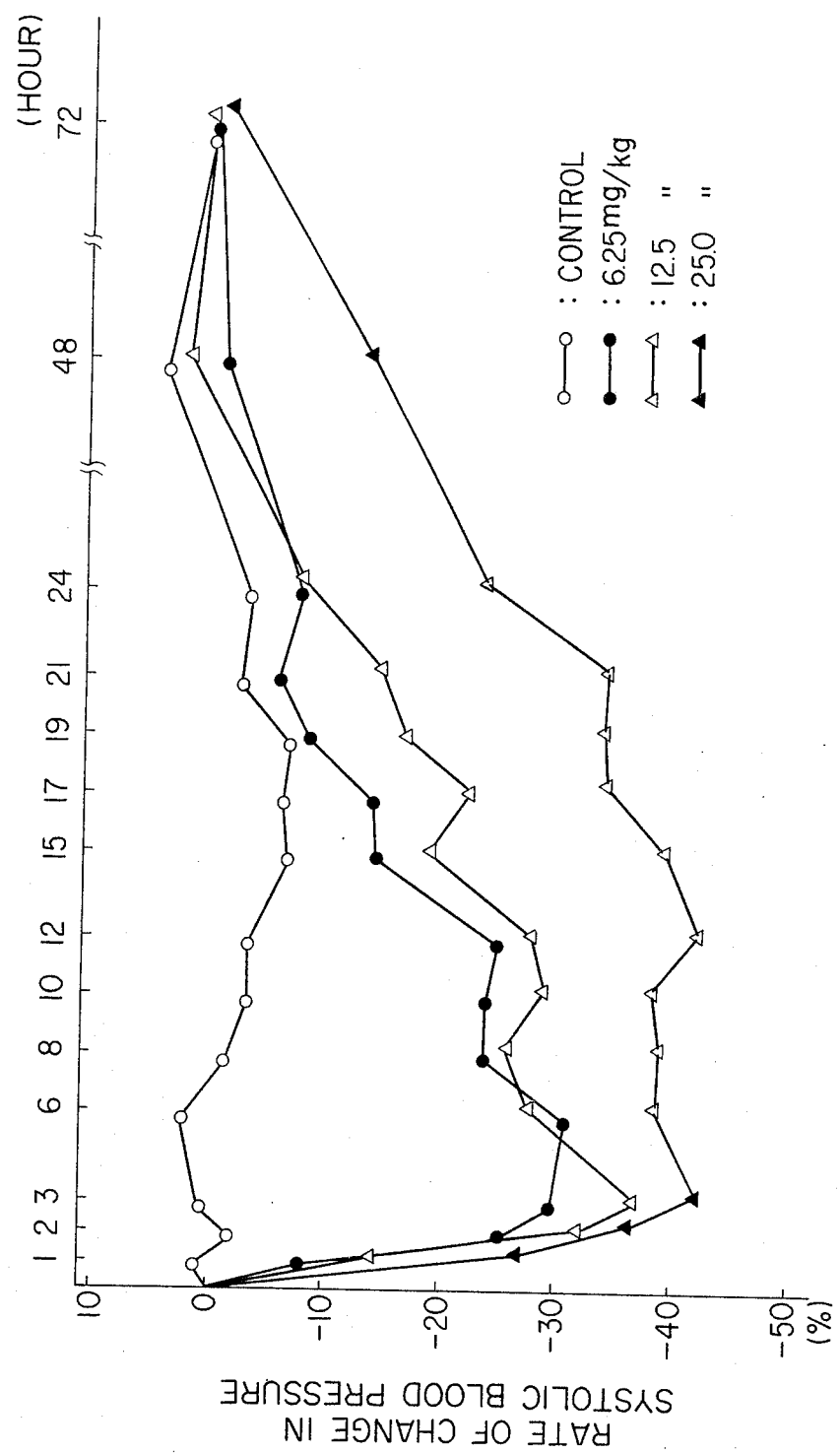

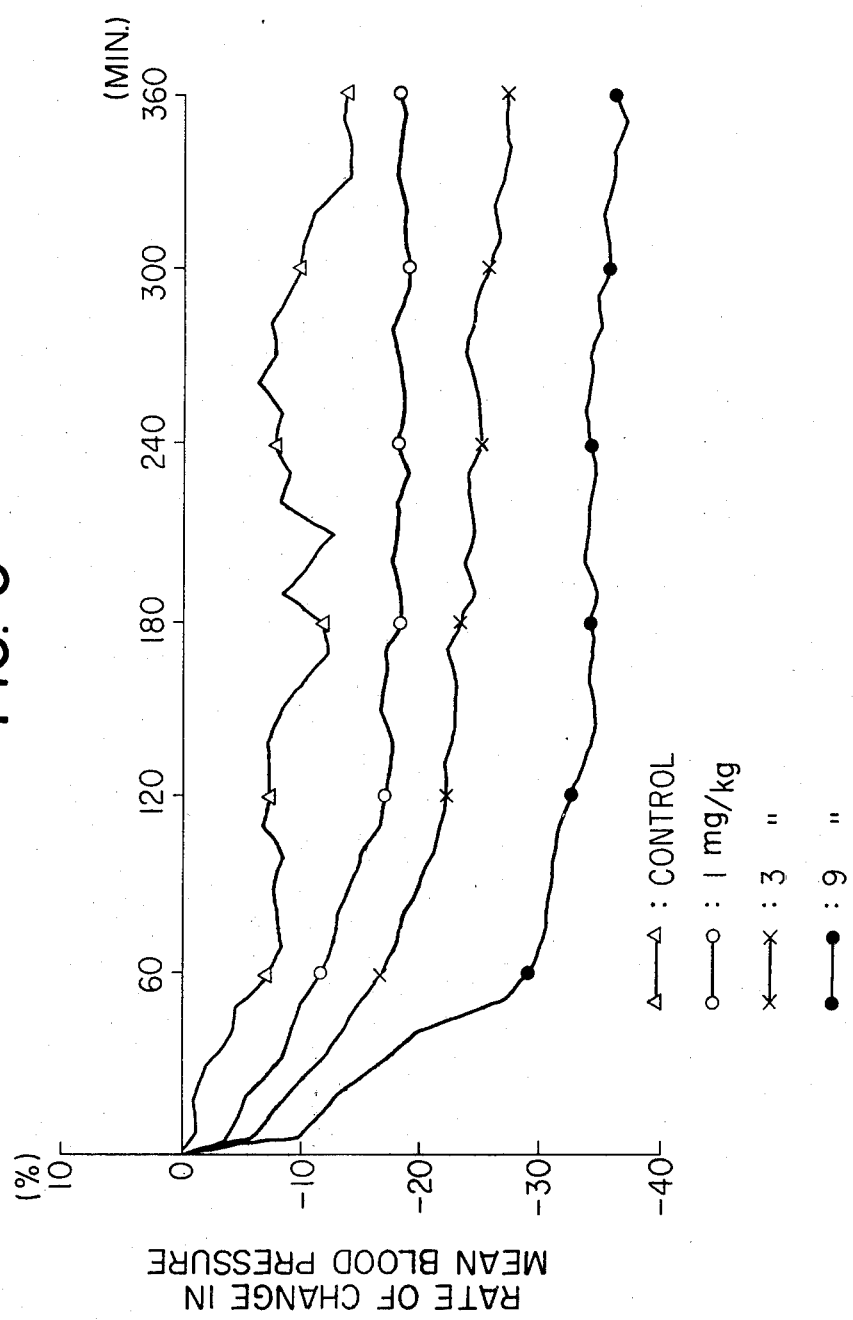

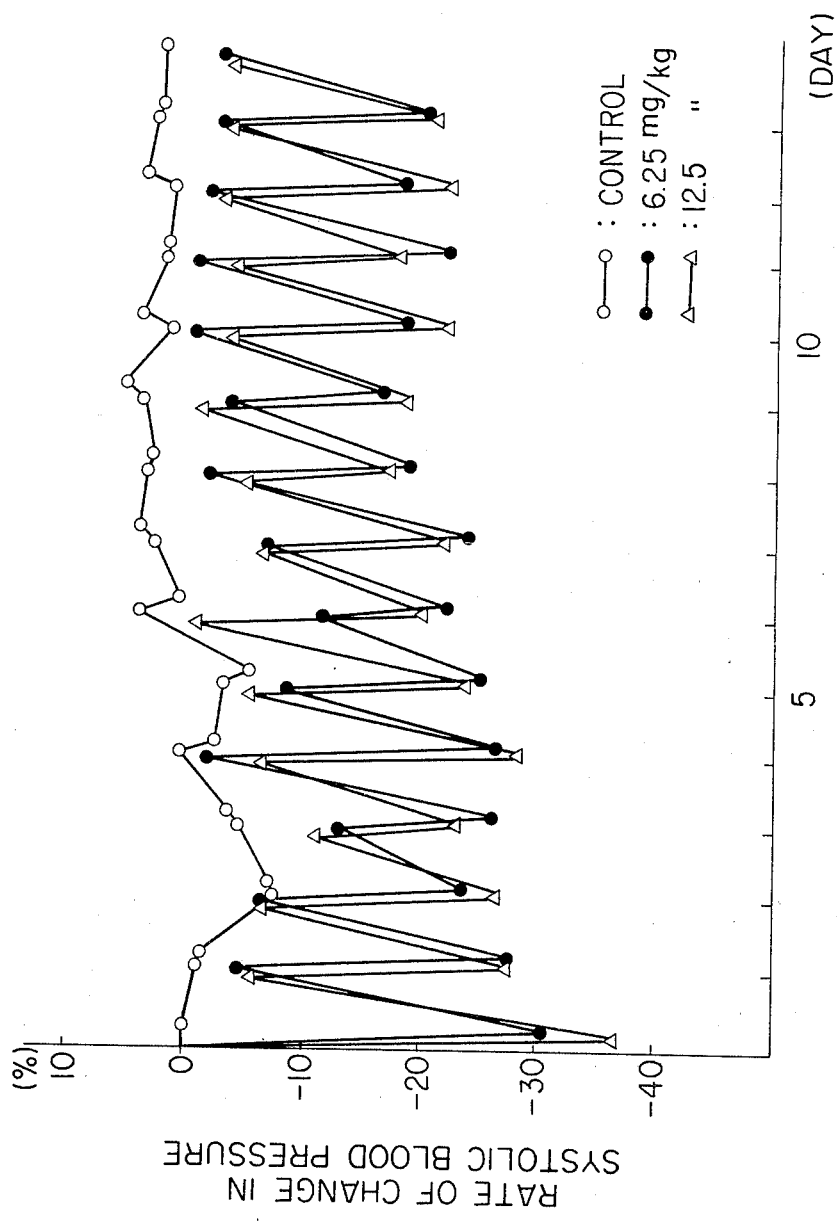

METHOD FOR TREATING HYPERTENSION WITH METHYLRESERPATE

BACKGROUND OF THE INVENTION

1. Field of the Invention

The present invention relates to a method of treating hypertension in human by orally administering an effective amount of methylreserpate of the formula (I):

(I)

The invention also relates to a pharmaceutical composition for treating hypertension in human. The composition comprises the above mentioned methylreserpate as the active ingredient and any other additive or excipient for oral administration.

2. State of the Art

Hypertension, along with cancer and heart disease, is one of the typical adult diseases and, as the number of aged persons increases so does the number of hypertensitive patients. Though therapy for hypertension is a very important problem, for various reasons no decisive method of treatment has been established.

Reserpine (hereinafter referred to as "RSP") and Rescinnamin (hereinafter referred to as "RCN"), which are Rauwolfia alkaloids, have long been used as remedies for hypertension because of their prolonged antihypertensive effect. However, their use is accompanied by unpleasant side effects such as uneasiness due to central nervous system depression, depressed state and loss of vitality. Thus, clinicans have been seeking RSP-type antihypertensive agents with little or no central nervous system depressive effect.

Methylreserpate (hereinafter referred to as "MR") was found in Rauwolfia Serpentina by Hoffmann et al. in 1954 [Helv. Chim. Acta., 37, 849 (1954)], and widely known as a metabolite of RSP [Dhar, M. M. et al.: J. Sci. Ind. Res., 140, 179 (1955); Glazko, A. J. et al.: J. Pharmacol. Exp. Therap., 118, 377 (1956); Dhar, M. M. et al.: Indian J. Pharmacy, 18, 293 (1956); Maggiolo, C. et al.: Proc. Soc. Exp. Biol. Med., 115, 149 (1964); and Huebner, C. F. et al.: J. Amer. Chem. Soc., 77, 469 (1955)].

Some researches were made on biologicl activity of this compound, and the following reports were made:

The substance exhibited no antihypertensive effect [Dhar, M. M. et al.: J. Sci. Ind. Res., 140, 179 (1955); Dhar, M. M. et al.: Indian J. Pharmacy, 18, 293 (1956); Bein, H. J.: Pharmacol. Rev., 8, 435 (1956); and Huebner, C. F. et al.: J. Amer. Chem. Soc., 77, 469 (1955)].

Inhibitory action of central nervous system was less than that of RSP [Dhar, M. M. et al.: J. Sci. Ind. Res., 140, 179 (1955); Indian J. Pharmacy, 18, 293 (1956); Bein, H. J.: Pharmacol. Rev., 8, 435 (1956); Huebner, C. F. et al.: J. Amer. Chem. Soc., 77, 469 (1955); Rubin, B. et al.: Fed. Proc., 13, 400 (1954); Dasgupta, S. R. et al.: Brit. J. Pharmacol., 12, 529 (1957); and Plummer, A. J. et al.: Fed. Proc., 13, 395 (1954)]. There was observed no decrease of serotonin in Brain [Brodie, B. B. et al.: Science, 123, 992 (1956)], increse of histamine [Sachdev, K. S. et al.: Arch. int. Pharmacodyn. Ther., 157, 14 (1965)] and slight decrease of noradrenaline in heart and adrenals [Creveling, C. R. et al.: J. Med. Chem. 11, 596 (1968)].

We investigated and confirmed first of all that MR is readily absorbed in the digestive tract. Then, based on our detailed study of the antihypertensive effect of MR on spontaneously hypertensive rats (SHR) and dogs, we have found that orally administered MR exhibits prolonged antihypertensive effect, and, though mild, has sufficient antihypertensive therapeutic activity. Finally, we investigated the toxicity and metabolism of MR, and confirmed that MR can be safely used as an antihypertensive medicine with little risk of central nervous system depression.

SUMMARY OF THE INVENTION

Accordingly, the object of the present invention is to provide a novel remedy for hypertension. Another object of the present invention is to provide an antihypertensive agent which can be repeatedly administered without risk of undesirable side effects.

MR, the effective ingredient of the present invention can be prepared by, for instance, simultaneously hydrolysing the 16- and 18-positions of reserpine and subsequently methylating the 16- position with diazomethane, or by solvolyzing the 18- position of reserpine with mixed solvent of methanol/cyclic ether or methanol alone [Helv. Chim. Acta., 37, 59 (1954); J. Med. Chem., 15 (No,6), 686–687 (1972)]. MR is a colorless or slightly yellow powder with a melting point between 237° and 239° C. (decomposing); and it is easily soluble in methanol, chloroform and ethanol, but hardly soluble in water.

DRAWINGS

FIG. 4 shows effect of MR on systolic blood pressure when administered orally;

FIG. 5 shows effect of MR on mean blood pressure of anesthesized dogs when administered by venous injection;

FIG. 7 shows effect of MR on systolic blood pressure of SHRs when administered orally and repeatedly;

DETAILED DESCRIPTION OF THE EMBODIMENTS

Dosage of the present medicine is, depending upon the sort and seriousness of hypertensive disease, usually 1 to 500 mg per day for a patient. Administration is oral, and any pharmaceutical preparation such as powder, table or capsule can be used.

For the preparation, it is acceptable to mix the ingredient with an inorganic excipient such as magnesium carbonate, anhydrous silicic acid, synthetic aluminum silicate or calcium phosphate, with an organic excipient such as lactose, corn starch or cellulose, or with any other conventional material.

The effect of MR, the effective ingredient of the present invention will be illustrated with practical data as follows:

EXAMPLE 1

(a) Antihypertensive Effect of MR by Single Administration (i) Effect on Blood Pressure of SHR The effect was examined through both direct and modified tail-cuff methods using male SHRs aged 25 to 30 weeks and weighing about 300 g.

In the direct cannulation method, polyethylene cannules were inserted in femoral arteries of the conscious unanesthesized SHRs under back-fixation, and MR solution was administered in an amount of 0.1 mg/100 g of weight for venous injection, and 1 ml/100 g of weight for oral administration. Changes in the blood pressure over 6 hours were measured with a multi-purpose polygraph RM-85 made by NIHON KODEN Co., Ltd. MR was dissolved in 0.9% NaCl aqueous solution with 1 N-HCl, and the solution was neutralized for use.

In the modified tail-cuff method, MR was dispersed in 0.2% carboxymethyl cellulose solution, and the suspension was orally administered (1 ml/100 g of weight), and then, changes in blood pressure over 72 hours were measured with a blood pressure recorder 8002 made by W+W Electronic.

Figure 1:
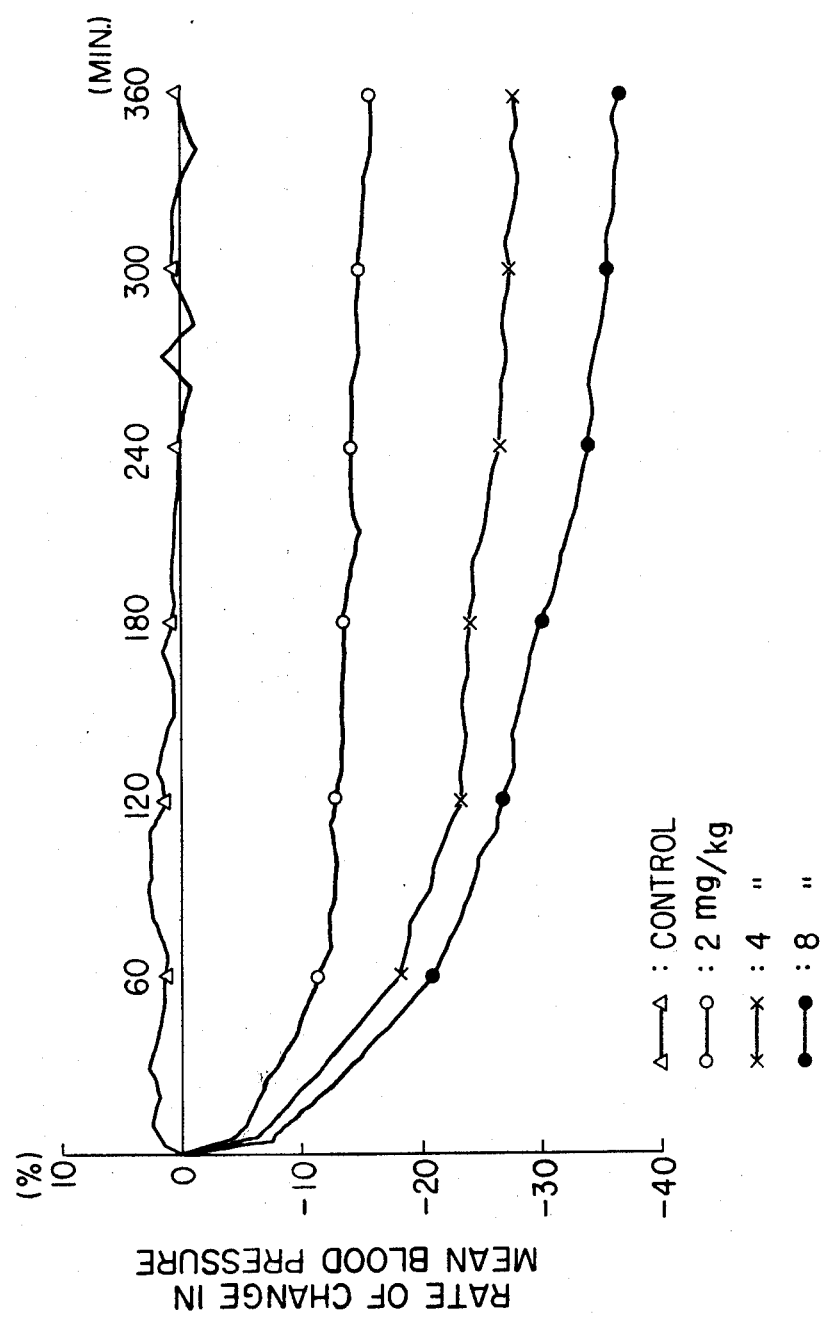
FIG. 1 shows effect of MR on mean blood pressure of SHRs when administered by venous injection.

When the measurements were made operatively after venous injection in the amounts of 2, 4 and 8 mg/kg, average rate of decrease in blood pressure was calculated from the depression area over a period of 6 hours (results are as shown in FIG. 1, 13%, 22.5% and 28%), and dose-related antihypertensive effect was observed. In every case, the effect observed was an immediate decrease in blood pressure after administration which continued for 4 to 5 hours, at which time blood pressure reached nearly level plateaus.

Figure 2:
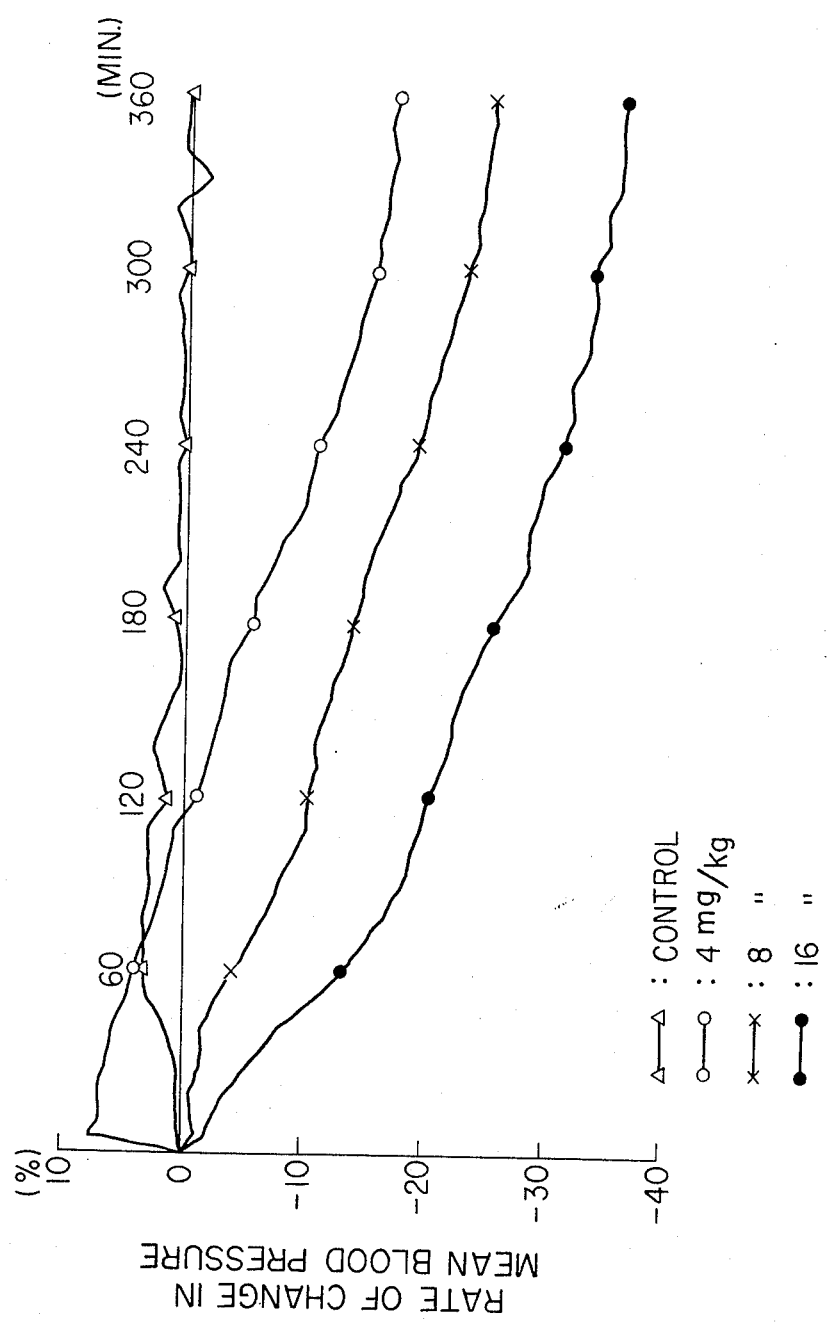
FIG. 2 shows effect of MR on mean blood pressure of SHRs when administered orally.

In the cases where 4, 8 and 16 mg/kg of MR were orally administered and where the measurements were made operatively, the same dose-related antihypertensive effect as obtained with the venous injection was observed as shown in FIG. 2. The observed effect was as follows:

in case of 4 mg/kg, blood pressure slowly decreased from 2 hours after the administration and the decrease reached 18% 6 hours after;

in the cases of 8 and 16 mg/kg, blood pressure gradually decreased from the administration and the decrease reached 26% and 37% respectively 6 hours after.

Figure 3:
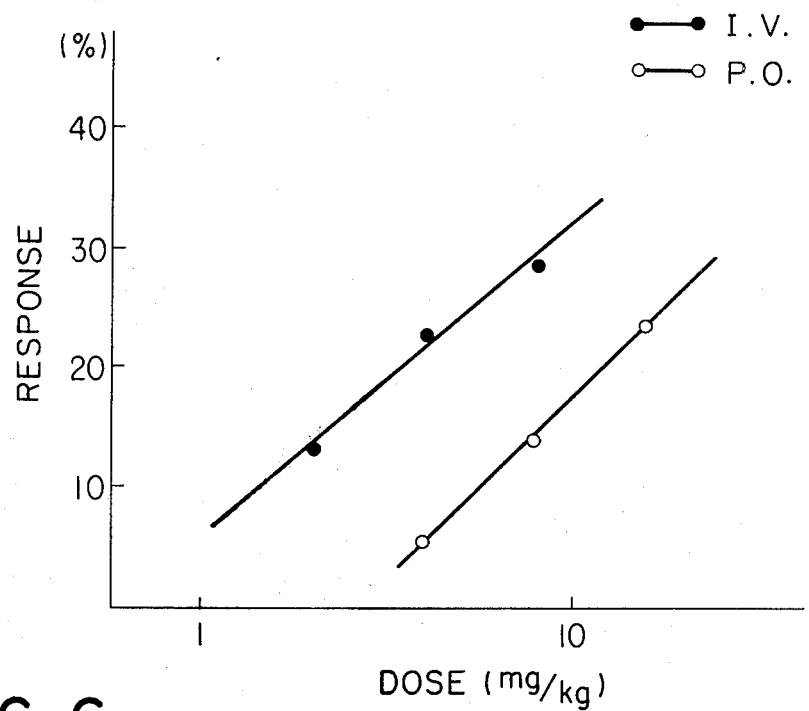
FIG. 3 shows dose-response curve of MR to SHRs.

The values of $DB_{20}$ (20% blood pressure descending dose) obtained from the dose-response curves of FIG. 3 were 3.5 mg/kg for the venous injection, and 11.9 mg/kg for the oral administration.

When MR was orally administered in the amounts of 6.25, 12.5 and 25.0 mg/kg and the measurements were made non-operatively, maximum rates of blood pressure decrease were, as shown in FIG. 4, 31.7%, 37.1% and 42.5% respectively, which correspond to dose-related antihypertensive effect. In every case, the observed effect was a decrease in blood pressure immediately after the administration and then, after 3 to 4 hours, went up to a plateau. The blood pressure gradually returned to its original level from about 12 hours after that, and reached its original level in 48 hours in the cases of 6.25 and 12.5 mg/kg, and in 72 hours in the case of 25 mg/kg.

(ii) Effect on Blood Pressure of Anesthesized Dogs

Male and female adult mongrel dogs weighing about 10 kg were anesthesized with sodium pentobarbital (35 mg/kg, venous injection), fixed at back position, and tracheal cannules were inserted by incision at cervical medial lines. Then, after insertion of polyethylene cannules in femoral arteries, MR solution was injected in an amount of 0.5 to 1 mg/kg through polyethylene cannules inserted in the branchial vein. Changes in blood pressure were measured for 6 hours after the administration with a multi-purpose polygraph RM-85 made by NIHON KODEN.

Figure 6:
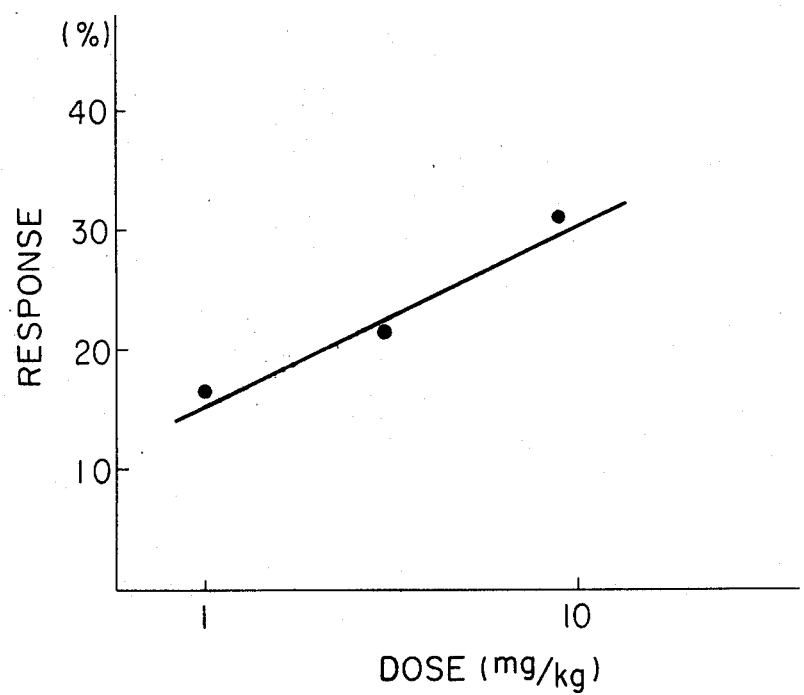
FIG. 6 shows dose-response curves of MR to anesthesized dogs.
Figure 8:
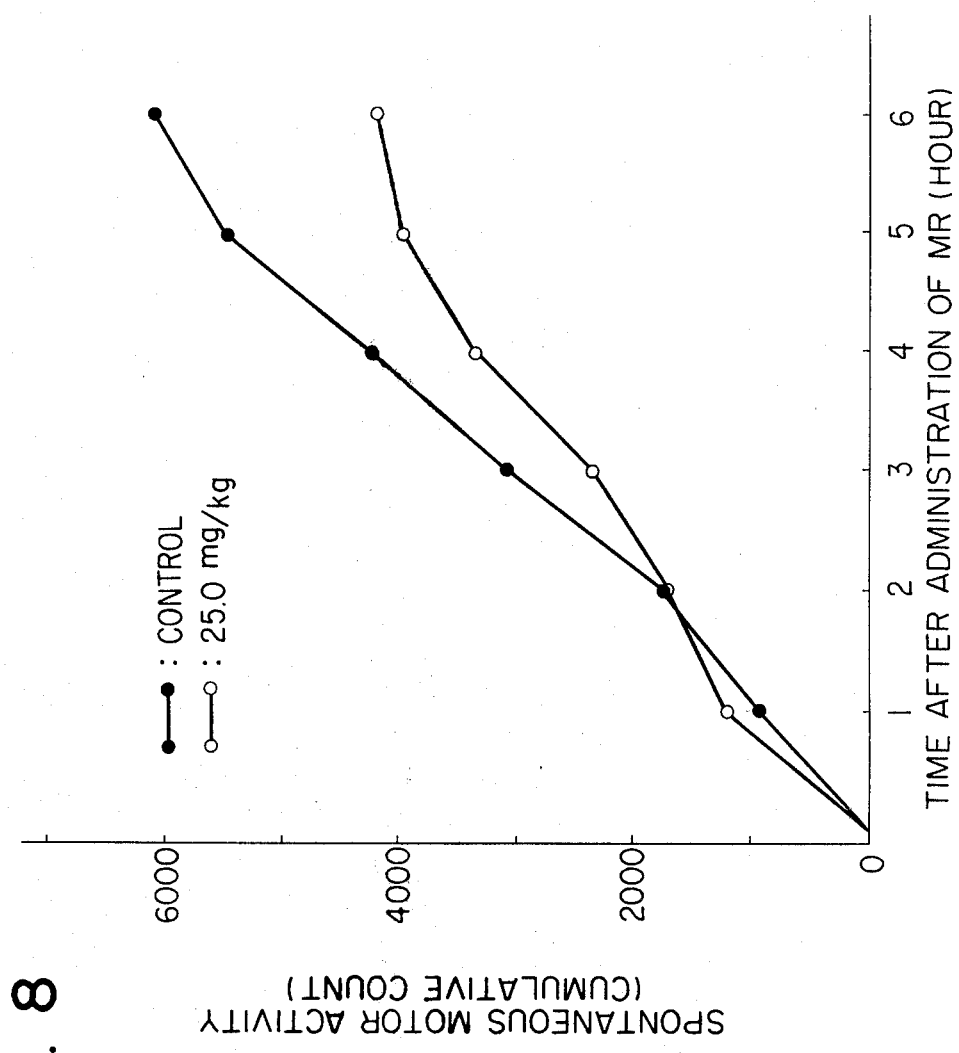
FIG. 8 shows effect of MR on spontaneous motor activity.

MR was dissolved in 0.9% NaCl aqueous solution with 1 N-HCl, and the solution was neutralized for use. In the cases where MR was intravenously injected in the amounts of 1, 3 and 9 mg/kg, average rates of blood pressure decrease calculated from depression area within 6 hours were 16.2, 22.3 and 35.1% respectively, and dose-related depressor effect was observed. The observed effect was a blood pressure decrease immediately after administration which came up nearly to plateau 2 hours after for 1 mg/kg, and 3 hours after for 3 mg/kg and 9 mg/kg, and in all cases remained on the plateau for 6 hours after that. The $DB_{20}$ value obtained from the dose-response curve of FIG. 6 was 2 mg/kg.

(b) Antihypertensive Effect of MR by Repeated Administration

The effect was determined through a direct cannulation by using male SHRs aged 25 to 30 weeks and weighing about 300 g. MR was suspended in 0.2% carboxymethyl cellulose solution and the suspension was orally administered (1 ml/100 g of weight) once a day over 2 weeks. Blood pressures were measured twice a day, just before and 4 hours after the administration with blood pressure recorder 8002 made by W+W Electronic.

Non-operative determination showed average rates of blood pressure decrease of 20 to 40% at 4 hours after the administration in every case, and 24 hours after the blood pressure had returned almost to the original level. Thus, the observed effect was nearly the same as the single administration over a term of 2 weeks.

From the fact that MR is the metabolite of RSP, it was cared that MR has no long lasting effect, which was proved by the above described pharmacological experiments of single administration and repeated administration to SHRs. Also, from the fact that, in the repeated administration, MR exhibited nearly constant antihypertensive effect over 2 weeks, it was found that MR has the characteristic of hardly giving tolerance as one of RSP-type medicine.

Because the effect of MR disappears more rapidly than that of RSP or the like, it will be understood that administration 2 to 3 times per day is necessary if used as an antihypertensive agent.

Table 1 shows the antihypertensive effect of MR in comparison with conventional hypertensive remedies. It is understood that the effect of MR, compared with that of RCN, is less intense when administered by venous injection, but almost the same when administered orally.

TABLE 1

Comparison of Effects of MR and Conventional Antihypertensive Remedies

| Medicines | Blood Pressure Decreasing Effect | |
|---|---|---|
| | $DB_{20}$ (mg/kg) P. O. | Rate of Effects I. V. |
| MR | 11.9 | 3.5 |
| | (1.00) | (1.00) |
| RSP | 3.8 | 0.2 |
| | (3.11) | (17.7) |
| RCN | 9.7 | 1.3 |
| | (1.22) | (2.70) |
| Dimethylaminoethyl reserpilinate dihydrochloride | 625.2 | 415.7 |
| | (0.02) | (0.01) |
| Hydralazine hydrochloride | 6.4 | 0.3 |
| | (1.85) | (11.7) |
| L-alpha-methyl-dopa | 1744 | 303.4 |
| | (0.01) | (0.01) |
| Hexamethonium chloride | 320.5 | 39.7 |
| | (0.04) | (0.08) |
| Trichlormethiazide | 149.9 | 79.8 |
| | (0.07) | (0.05) |

In order to prove that MR is a medicine of high safety, experimental results on side effect and toxicity will be shown below.

EXAMPLE 2 Effects on Central Nervous System

MR was suspended in 0.2% carboxymethyl cellulose solution, and the suspension was orally administered to male mice of dd-strain weighing 23 to 27 g in an amount of 1 ml/100 g of weight.

Effects on central nervous system were studied as follows:

(a) Effect on Spontaneous Motor Activity 25 mg/kg of MR were administered to the mice. After 15 minutes of letting them alone, spontaneous motor activity over 6 hours was measured hourly with an "Animex" made by AB Farad. The administration of MR tended to supress spontaneous motor activity from 3 hours after the administration, and no significant difference ($P=0.05$) was observed in average suppressive effect among four groups of five mice each.

(b) Effect on Hexobarbital Hypnosis

MR was administered to 10 mice per one group in the amounts of 12.5 mg/kg or 25 mg/kg, and 6 hours later, 100 mg/kg of sodium hexobarbital were intraperitoneally injected. Period of induced sleeping was measured with righting reflex as a parameter.

MR did not influence, as seen from Table 2, the time required to induce sleep nor the sleeping period.

TABLE 2

Effect of MR on Hexobarbitol Hypnosis

| | Hypnotic Time (sec.) | Sleeping Time (min.) |
|---|---|---|
| Control Group | 151±7 | 34.4±3.1 |
| Group of 12.5 mg/kg | 144±7 | 32.9±4.4 |
| Group of 25 mg/kg | 159±7 | 34.2±6.7 |

(c) Effect on Body Temperature 25 mg/kg of MR was administered to 10 mice per one group, and rectal temperatures were measured with Thermister-Thermometer MGA-III-219 made by NIHON KODEN Co., Ltd. Administration of MR resulted in, as shown in Table 3, a slight decrease in the temperature 3 hours after the administration.

TABLE 3

Effect of MR on Body Temperature

| | After Administration | | |
|---|---|---|---|
| | 1 Hour | 2 Hours | 3 Hours |
| Control Group | 36.3±0.2° C. | 36.4±0.1° C. | 36.2±0.2° C. |
| Group of 25 mg/kg | 36.6±0.2° C. | 36.2±0.2° C. | 35.6±0.1° C. |

(c) Effect on Motorability 25 mg/kg of MR were administered to 10 mice per one group. The mice were put on a wooden bar of 2 cm diameter which rotated at 10 r.p.m., and the number of mice which fell down from the bar was counted.

Administration of MR showed, as seen from Table 4, slight suppression of motorability 3 hours after the administration.

TABLE 4

Effect of MR on Motorability

| | Number of Animals Examined | Number of Animals that fell After Administration | | |
|---|---|---|---|---|
| | | 1 Hour | 2 Hours | 3 Hours |
| Control Group | 10 | 0 | 1 | 1 |
| Group of 25 mg/kg | 10 | 0 | 2 | 4 |

From the above described behavior-pharmacological studies it can be said that the central nervous system depressing effect of MR is weaker than that of RSP.

EXAMPLE 3 Acute Toxicity

Table 5 shows acute toxicity of MR to mice and rats determined by a conventional testing method.

As seen from the Table, values of $LD_{50}$ in the case of oral administration to mouse and rat are 210 mg/kg and 479 mg/kg respectively, which are about 10,000 times and about 24,000 times the clinical dosage of RCN having the effect nearly equal to MR. Thus, MR is considered to be a very safe medicine.

TABLE 5

Acute Toxicity of MR

| Animal | Sex | Route of Administration | $LD_{50}$ (mg/kg) |
|---|---|---|---|
| Mouse | male | P. O. | 210 |
| Mouse | female | I. V. | 48 |
| Rat | male | P. O. | 479 |

EXAMPLE 4 Sub-Acute Toxicity of MR

Test of Oral Sub-Acute Toxicity in Rats

Animal used, breeding conditions and method of administration:

Male rats of SD (SPF) strain aged 4 weeks were purchased and, after breeding for 10 days, those weighing 146 to 150 g were selected to form groups of 10 rats. The rate were bred in individual cages under the following conditions: temperature, 23°±2° C.; relative humidity, 55±5%; free taking of solid food (CE-2, CLEA Japan, Inc.) and tap water.

The medicine was prepared by grinding MR in a mortar to fine powder and by turning to suspension in 0.2% carboxymethyl cellulose solution when used, and administered orally through a metallic stomach tube for rats. Volume of the medicine solution for one administration was dicided to be 1 ml per 100 g of weight, and the dose was administered once a day, 6 times a week over 5 weeks. The control group received the same volume of 0.2% carboxymethyl cellulose solution. Dosages were set at 5 levels: 12.5 mg/kg, 25 mg/kg, 50 mg/kg, 100 mg/kg and 200 mg/kg, which correspond respectively to 625, 1250, 2500, 5000 and 10000 times the daily clinical dosage of RCN having the equal effect to MR.

(i) Observation of General Symptoms, Body Weight, Food-Intake and Water-Intake All the rats were observed daily and general symptoms noted. Weight was measured daily, average food-intake once every three days, and average water-intake once every two days.

From about the 15th day for the group administered 50 mg/kg, and from about the 10th day for the group administered 100 mg/kg, blepharoptosis, roughening of fur and dirtiness of public region were observed. In the group administered 200 mg/kg, there was observed, in addition to the above symptoms, reduction of body weight, bloody cojunctival discharge, and a decrease of limb-skin temperature. All the animals died between the 2nd and 17th days, many dying 2 to 4 hours after administration.

Figure 9:
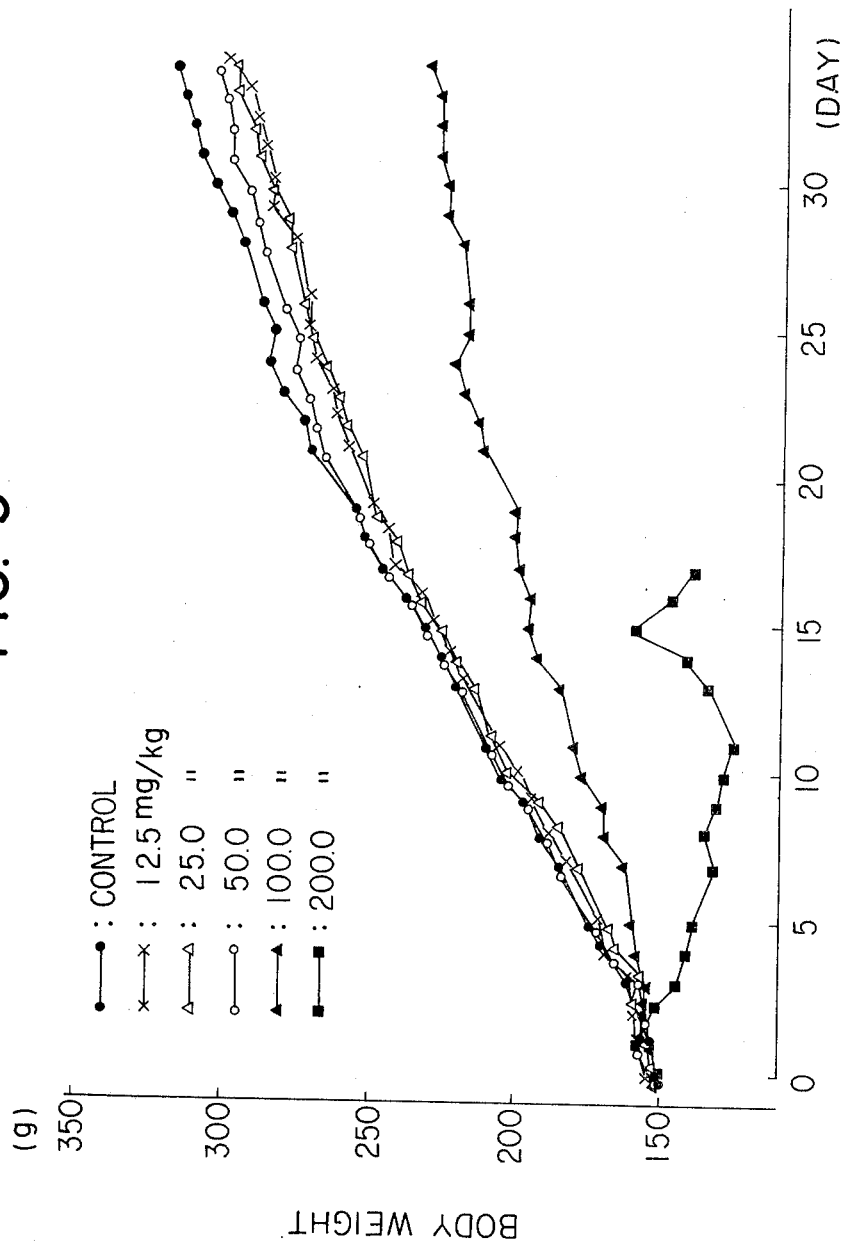
FIG. 9 shows weight changes of rats in oral subacute toxicity test of MR.
Figure 10:
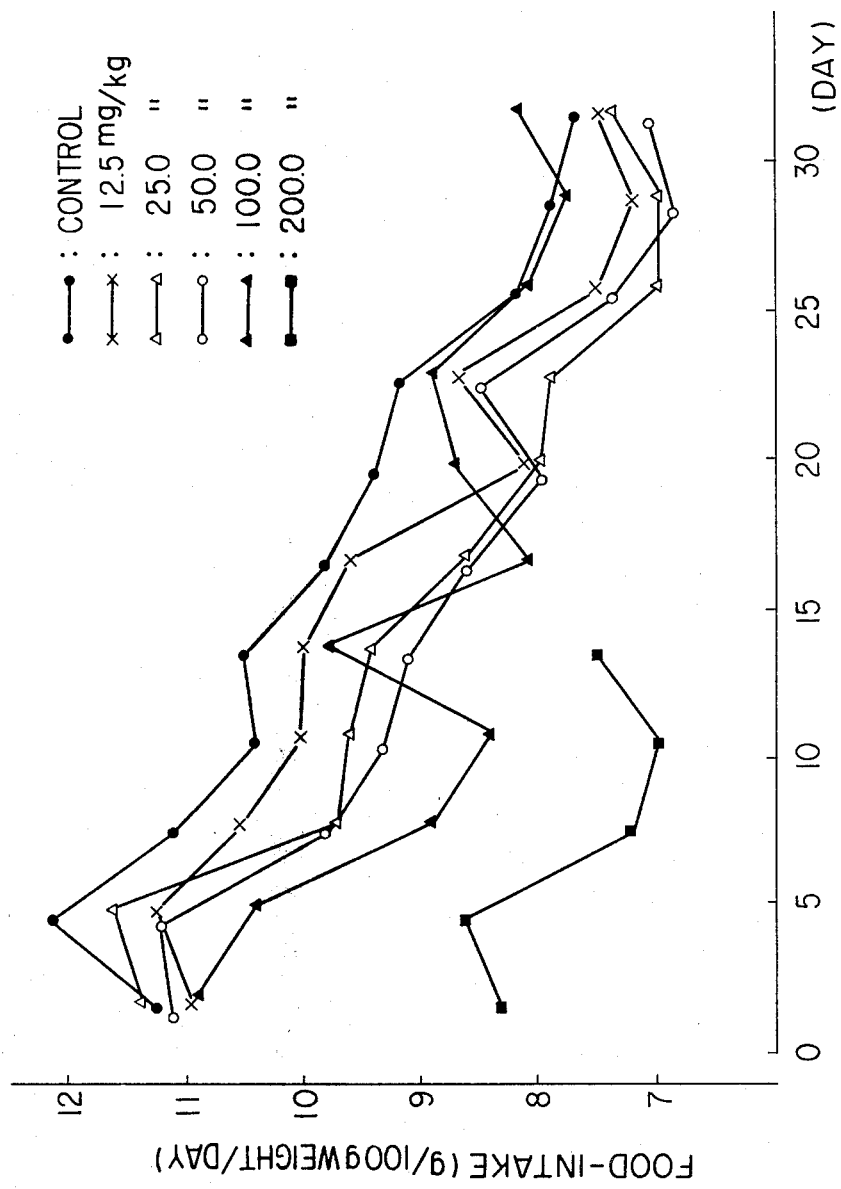
FIG. 10 shows changes of food-intake by rats in oral sub-acute toxicity test of MR.
Figure 11:
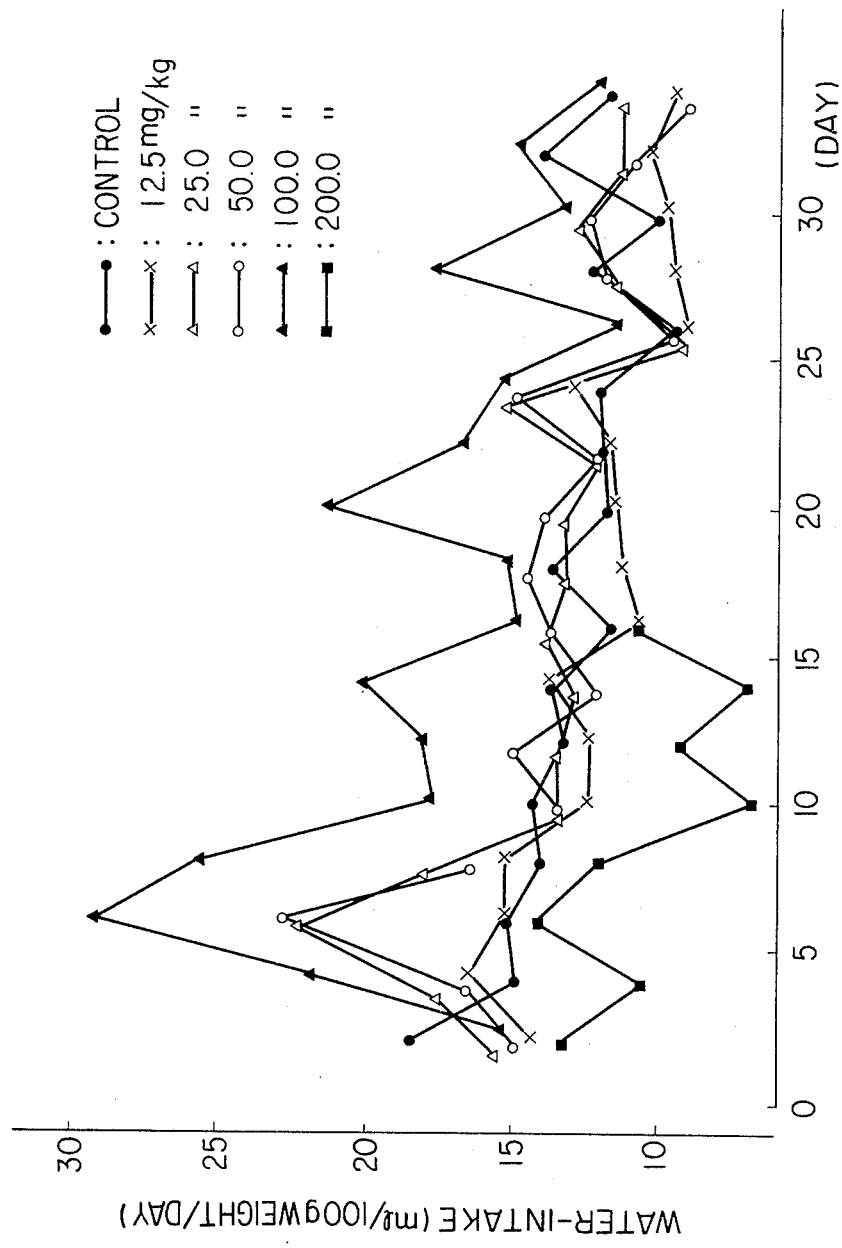
FIG. 11 shows changes of water-intake by rats in oral sub-acute toxicity test of MR.

Measured values of body weight, food-intake and water-intake are shown in FIGS. 9 to 11. There was no change in weight in the 12.5 mg/kg group, the 25 mg/kg group and the 50 mg/kg group throughout the testing period. On the other hand, in the 100 mg/kg group there was observed a tendency toward inhibition of weight gain which increased in intensity with time beginning shortly after administration; and in the 200 mg/kg group decrese of weight. No difference was observed in food-intake in comparison with the control group except for the 200 mg/kg group. Water-intake increased a little for the 100 mg/kg group, but there was no change for the other groups.

(ii) Hematological Examinations

On the 10th day, the 20th day and the 30th day measurements were made as follows: red blood cell count and white blood cell cont (with a Celloscope 401, AB Larsljungberg & Co.); hematocrit value (capillary method by high-speed centrifuge); hemoglobin value (cyanmetohemoglobin method); platelet count (Toa Platelet Counter PL-100); and hemogramme (Giemsas-taining). The results are given in Table 6. In the 100 mg/kg group and the 200 mg/kg group there was observed an increase in red cell count and a decrease in white cell count, but no significant change was observed in the other groups throughout the testing period.

TABLE 6
Hematological Observation in Rats Treated Orally with MR for 30 Days

| | No. of Rats | Days of Treatment | R.B.C. ($\times 10^4$/mm$^3$) | W.B.C ($\times 10^2$/mm$^3$) | Platelet ($\times 10^3$/mm$^3$) | Hb. (g/dl) | Ht. (%) | Differentiation of W.B.C. (%) | | | |
|---|---|---|---|---|---|---|---|---|---|---|---|
| | | | | | | | | Neutro. | Eosino. | Lymph. | Mono. |
| Control | 9 | 10 | 768±17.8 | 162±7.3 | 760±52.8 | 14.8±0.15 | 50.6±1.42 | 15.1±1.4 | 1.7±0.3 | 73.6±8.3 | 2.6±0.4 |
| Control | 10 | 20 | 849±9.9 | 174±10.9 | 856±30.1 | 13.3±0.63 | 51.5±1.43 | 17.6±1.9 | 1.7±0.4 | 78.2±2.1 | 2.5±0.3 |
| Control | 10 | 30 | 895±13.7 | 154±9.6 | 682±30.1 | 13.4±0.25 | 50.1±0.56 | 16.2±1.9 | 1.6±0.3 | 80.7±1.8 | 1.6±0.3 |
| 12.5 mg/kg | 10 | 10 | 770±15.1 | 151±7.2 | 816±49.4 | 14.5±0.37 | 52.4±1.10 | 15.7±1.8 | 1.6±0.4 | 80.6±1.7 | 2.1±0.2 |
| 12.5 mg/kg | 10 | 20 | 879±12.6 | 168±5.6 | 866±41.4 | 13.2±0.53 | 54.5±0.97 | 19.4±2.1 | 2.4±0.5 | 76.4±2.1 | 1.8±0.4 |
| 12.5 mg/kg | 10 | 30 | 890±8.4 | 163±9.4 | 643±43.9 | 14.5±0.29 | 50.2±0.55 | 18.1±1.8 | 2.4±0.5 | 78.3±1.9 | 1.2±0.3 |
| 25.0 mg/kg | 10 | 10 | 774±16.4 | 161±7.8 | 853±32.6 | 14.2±0.65 | 52.4±1.01 | 14.6±1.6 | 1.5±0.3 | 81.8±2.0 | 2.1±0.4 |
| 25.0 mg/kg | 10 | 20 | 872±22.0 | 179±12.8 | 834±42.5 | 13.0±0.61 | 51.9±0.56 | 22.8±2.2 | 1.8±0.4 | 74.8±2.1 | 1.2±0.3 |
| 25.0 mg/kg | 10 | 30 | 913±8.7 | 140±6.5 | 658±26.8 | 13.3±0.52 | 49.8±0.52 | 19.2±1.9 | 1.4±0.6 | 78.0±2.0 | 1.5±0.5 |
| 50.0 mg/kg | 10 | 10 | 771±10.8 | 143±10.5 | 861±33.5 | 14.1±0.40 | 52.2±0.92 | 13.5±0.8 | 1.8±0.4 | 82.3±1.1 | 2.4±0.3 |
| 50.0 mg/kg | 10 | 20 | 864±19.8 | 162±9.9 | 834±37.1 | 13.8±0.33 | 52.6±0.86 | 22.1±2.2 | 1.3±0.4 | 75.0±2.3 | 1.6±0.3 |
| 50.0 mg/kg | 10 | 30 | 901±15.1 | 153±12.5 | 656±36.7 | 14.7±0.42* | 50.8±0.53 | 17.5±1.8 | 2.6±0.5 | 78.7±1.8 | 1.2±0.2 |
| 100.0 mg/kg | 10 | 10 | 805±17.3 | 116±5.8* | 782±31.2 | 15.1±0.58 | 52.8±0.74 | 18.3±2.3 | 2.3±0.5 | 77.1±2.2 | 2.3±0.3 |
| 100.0 mg/kg | 10 | 20 | 908±17.2* | 145±9.2 | 862±22.5 | 13.8±0.35 | 52.9±0.99 | 27.6±2.9 | 1.2±0.3 | 69.6±3.0 | 1.6±0.3 |
| 100.0 mg/kg | 10 | 30 | 915±15.1 | 142±7.2 | 696±13.9 | 13.6±0.26 | 51.0±0.93 | 21.9±1.9 | 1.4±0.4 | 75.2±1.6 | 1.5±0.3 |
| 200.0 mg/kg | 4 | 10 | 877±69.2* | 115±19.1* | 592±54.7 | 18.3±1.63* | 56.6±3.50 | 61.8±12 | 0.8±0.5 | 36.3±12 | 1.3±0.5 |
| 200.0 mg/kg | 0 | 20 | — | — | — | — | — | — | — | — | — |
| 200.0 mg/kg | 0 | 30 | — | — | — | — | — | — | — | — | — |

TABLE 6-continued (×10 Hematological Observation in Rats Treated Orally with MR for 30 Days)

| No. of Rats | Days of Treatment | R.B.C. (x10⁴/mm³) | W.B.C (×10²/mm³) | Platelet (×10³/mm³) | Hb. (g/dl) | Ht. (%) | Differentiation of W.B.C. (%) | | | |
|---|---|---|---|---|---|---|---|---|---|---|
| | | | | | | | Neutro. | Eosino. | Lymph. | Mono. |
| mg/kg | | | | | | | | | | |

*Significant difference from control (P 0.05).
The values represent mean ± standard error.

(iii) Urianalysis

Urinanalysis was conducted on the last day of the repeated administration as to pH, protein content, glucose content, ketone body content and occult blood by testing paper methods. (Labstix, Miles-Sankyo Co., Ltd.)

As seen from Table 7, the results do not indicate abnormal feature any worth special mention.

Figure 12:
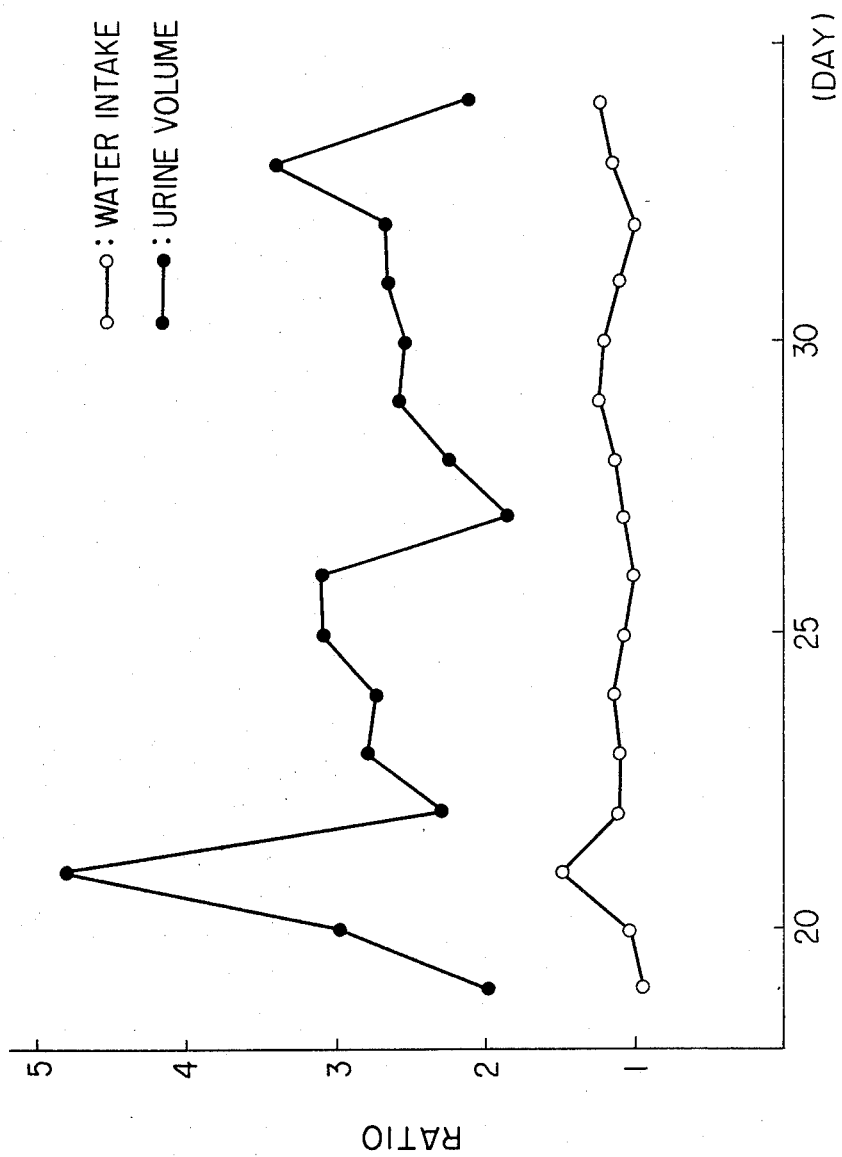
FIG. 12 shows changes of urine volume and water-intake by rats of 100 mg/kg group in oral sub-acute toxicity test of MR.

FIG. 12 shows daily amounts of urine of 10 animals of 100 mg/kg group and of 5 animals of the control group from the 19th day of the administration. The urine volume of the 100 mg/kg group was about 2 to 3 times the volume of the control group.

TABLE 7

Urianalysis in 10 Rats treated with MR for 30 days (Sub-Acute Toxicity)

| | | Number of Rats | | | | |
|---|---|---|---|---|---|---|
| | | Control | 12.5 mg/kg | 25.0 mg/kg | 50.0 mg/kg | 100.0 mg/kg |
| pH | 6 | 3 | 3 | 2 | 1 | 2 |
| | 7 | 5 | 4 | 7 | 7 | 7 |
| | 8 | 2 | 3 | 1 | 2 | 1 |
| Protein | − | 1 | 0 | 0 | 0 | 1 |
| | + | 5 | 5 | 6 | 6 | 3 |
| | ++ | 4 | 3 | 4 | 4 | 3 |
| | +++ | 0 | 2 | 0 | 0 | 3 |
| Glucose | − | 10 | 10 | 10 | 10 | 10 |
| Ketone Body | − | 10 | 10 | 10 | 9 | 9 |
| | + | 0 | 0 | 0 | 1 | 1 |
| Occult Blood | − | 10 | 10 | 10 | 10 | 10 |

(iv) Serum-Biochemical Examination

After the final administration followed by 24 hours fast, the following analyses were made: Glucose (by o-toluidine-boric acid method); Total Protein (by biurett method); Blood Uria Nitrogen (diacetyl monoxime method); GOT and GPT Activities (Reitman-Frankel method); Alkaline Phosphatase Activity (Kind-King method); and Sodium and Potassium Content (flame-photometer).

The results are shown in Table 8. There was observed decrease of glucose value in the 50 mg/kg group and the 100 mg/kg group. The results of the other determination were, though there were certain fluctuations, all within the scope of normal values.

TABLE 8

Serum Biochemical Analysis of Rats Treated Orally with MR for 30 Days

| | Control | | 12.5mg/kg | | 25.0mg/kg | | 50.0mg/kg | | 100.0mg/kg | |
|---|---|---|---|---|---|---|---|---|---|---|
| | No. of Rats | Mean±S.E. | No. of Rats | Mean±S.E. | No. of Rats | Mean±S.E. | No. of Rats | Mean±S.E. | No. of Rats | Mean±S.E. |
| Total Protein (g/dl) | 10 | 6.94±0.16 | 10 | 7.06±0.09 | 10 | 6.65±0.08 | 10 | 6.76±0.18 | 9 | 6.57±0.28 |
| GOT (K.U.) | 10 | 86.7±5.42 | 10 | 80.4±7.55 | 9 | 92.2±8.74 | 10 | 117.1±10.48* | 10 | 114.9±7.02* |
| GPT (K.U.) | 10 | 34.2±1.02 | 10 | 32.0±1.16 | 9 | 36.6±1.55 | 10 | 38.8±2.21 | 9 | 32.7±1.67 |
| ALP (K.A.U.) | 10 | 20.6±1.60 | 9 | 18.8±10.82 | 10 | 17.0±0.93 | 10 | 18.7±1.39 | 9 | 22.7±2.91 |
| Glucose (mg/dl) | 10 | 147.7±3.33 | 10 | 149.3±3.36 | 9 | 155.4±6.06 | 9 | 113.7±5.25* | 9 | 100.5±8.60* |
| BUN (mg/dl) | 10 | 13.6±0.64 | 10 | 14.6±0.35 | 8 | 15.7±0.77 | 9 | 17.2±0.56* | 8 | 17.5±1.01* |
| Na³⁰ (mEq/l) | 10 | 145.7±0.89 | 10 | 148.9±1.59 | 9 | 146.9±2.08 | 8 | 147.4±1.01 | 8 | 148.6±1.40 |
| K⁺(mEq/l) | 10 | 4.53±0.10 | 10 | 4.53±0.11 | 9 | 4.65±0.09 | 8 | 4.76±0.13 | 8 | 4.86±0.12 |

*Significant difference from control (P<0.05)

(v) Histopathological Examination

Rats were sacrificed under anesthesia with ether. After observation of gross appearance of all the organs, extraction and weighing were made on spleen, lung, liver, adrenal, heart, thymus, kidney, testicles, hypophysis and thyroid. In addition to the above organs, femoral bone marrow, lymph node, stomach, intestine, pancreas, urinary bladder, prostate and central nervous system were removed and fixed in 10% formaline solution.

Five samples were randomly selected from each group, and paraffin-sectioned preparations of the organs were made by a routine method. The preparations were stained with hematoxyline-eosin stain and Luxol-fast blue (central nervous system only) and examined histopathologically.

There was no noteworthy change as to the gross appearance of the organs of the subject animals.

Table 9 and Table 10 show recorded absolute organ weights and relative organ weights. With respect to the absolute weights, weight increase of adrenal was observed in 25 mg/kg group and 50 mg/kg group. The group of 100 mg/kg administration had, in addition to the above change, decrease in weight of the other organs. As to the relative weights, though there were certain differences between the administered groups and the control group, no significant difference was noted on the whole.

The histological findings are as follows; and the findings on each rat are as given in Table 11. Spleen: 5/5 rats of the 200 mg/kg group had slight to moderate atrophy, and 4/5 rats of the 100 mg/kg group had slight to moderate congestion.

Bone Marrow: The examination was made on femoral bone marrow. Moderate hypoplasia was observed in 2/2 rats of the 200 mg/kg group, and slight hypoplasia in 3/5 rats of the 100 mg/kg group.

Lung: A change like interstetitial pneumonia was observed in 5/5 rats of the 200 mg/kg group, and among them, 2/5 rats had marked congestion.

Liver: In 5/5 rats of the 200 mg/kg group, there was observed necrosis and collapse or vacuolation of liver cells at central zone of the lobules. In some of the rats, inclusive of the control group, there were found here and there lymphocytic cell infiltration in Glisson's capsule or liver cell cords, and swelling of Kupffer cells.

Adrenal: 1/5 rat of the 25 mg/kg group, 5/5 rats of the 50 mg/kg group and 100 mg/kg group, and 1/5 rat of the 200 mg/kg group had cortical hypertrophy.

Heart: Some of the rats including the control group had focal collapse of heart muscles.

Thymus: Marked atrophy was observed in 2/2 rats of the 200 mg/kg group.

No other pathological change was found in the other organs: lymph mode, stomach, intestine, pancreas, kidney, urinary bladder, testicle, prostate, hypophysis, thyroid and central nervous system.

TABLE 9

| Organ | | Absolute Organ weights of Rats Treated Orally with MR | | | | |
|---|---|---|---|---|---|---|
| | | Control | 12.5mg/kg | 25.0mg/kg | 50.0mg/kg | 100.0mg/kg |
| Heart | (g) | 1.17±0.03 | 1.15±0.04 | 1.26±0.03 | 1.34±0.07 | 1.16±0.04 |
| Spleen | (g) | 0.64±0.03 | 0.69±0.03 | 0.71±0.03 | 0.73±0.03 | 0.56±0.03 |
| Lung | (g) | 2.24±0.12 | 1.32±0.12 | 2.35±0.05 | 2.26±0.10 | 2.10±0.06* |
| Liver | (g) | 10.12±0.47 | 10.18±0.50 | 10.00±0.47 | 10.16±0.33 | 7.55±0.32* |
| Kidney | (g) | 1.18±0.04 | 1.17±0.05 | 1.20±0.04 | 1.19±0.03 | 0.89±0.03** |
| Brain | (g) | 2.28±0.03 | 2.28±0.03 | 2.26±0.04 | 2.26±0.03 | 2.17±0.04* |
| Thymus | (g) | 0.59±0.03 | 0.63±0.04 | 0.54±0.02 | 0.58±0.05 | 0.39±0.03** |
| Testis | (g) | 1.60±0.03 | 1.63±0.05 | 1.71±0.10 | 1.68±0.03 | 1.51±0.09 |
| Salivary | (g) | 0.31±0.01 | 0.27±0.01 | 0.26±0.01** | 0.26±0.01* | 0.21±0.01** |
| Adrenal | (mg) | 24.55±0.96 | 24.95±1.42 | 27.86±1.69 | 33.17±2.22 | 34.92±1.38** |
| Thyroid | (mg) | 9.19±0.39 | 8.59±0.50 | 10.07±0.55 | 8.55±0.50 | 7.86±0.38 |
| Hypophysis | (mg) | 10.77±0.62 | 10.60±0.41 | 11.98±0.44 | 11.93±0.48 | 10.46±0.17 |

*Significant difference from control (P<0.05).
**Significant difference from control (P<0.01)
The values represent mean±standard error.

TABLE 10

| Organ | | Relative Organ Weights of Rats Treated Orally with MR | | | | |
|---|---|---|---|---|---|---|
| | | Control | 12.5mg/kg | 25.0mg/kg | 50.0mg/kg | 100.0mg/kg |
| Heart | (g) | 0.41±0.01 | 0.42±0.01 | 0.44±0.01 | 0.48±0.02* | 0.55±0.02** |
| Spleen | (g) | 0.22±0.01 | 0.25±0.01** | 0.25±0.01* | 0.26±0.01 | 0.26±0.01** |
| Lung | (g) | 0.84±0.05 | 0.84±0.04 | 0.82±0.03 | 0.93±0.04 | 0.99±0.02 |
| Liver | (g) | 3.46±0.07 | 3.67±0.11 | 3.46±0.17 | 3.62±0.14 | 3.57±0.14 |
| Kidney | (g) | 0.41±0.01 | 0.42±0.01 | 0.42±0.01 | 0.42±0.01 | 0.42±0.01 |
| Brain | (g) | 0.79±0.02 | 0.83±0.03 | 0.79±0.02 | 0.81±0.03 | 1.03±0.03** |
| Thymus | (g) | 0.21±0.01 | 0.23±0.02 | 0.23±0.01 | 0.21±0.02 | 0.19±0.01 |
| Testis | (g) | 0.6±0.02 | 0.59±0.01 | 0.65±0.05 | 0.60±0.02 | 0.73±0.03** |
| Salivary | (g) | 0.11±0.00 | 0.11±0.00 | 0.09±0.00* | 0.10±0.00 | |
| Adrenal | (mg) | 8.42±0.18 | 9.01±0.47 | 9.67±0.42 | 11.75±0.77 | 16.60±0.82 |
| Thyroid | (mg) | 3.18±0.15 | 3.10±0.17 | 3.53±0.19 | 3.04±0.18 | 3.71±0.09** |
| Hypophysis | (mg) | 3.68±0.13 | 3.79±0.11 | 4.15±0.12* | 4.20±0.10** | 4.98±0.19** |

*Significant difference from control (P<0.05).
**Significant difference from control (P<0.01).
The values represent mean±standard error.
Organ weight/100g weight

TABLE 11-A

| | | | Histopathological Findings of Rats Treated Orally with MR | | | | | | | | | | | | | | |
|---|---|---|---|---|---|---|---|---|---|---|---|---|---|---|---|---|---|
| | | | Identification Nos. | | | | | | | | | | | | | | |
| | | | Control | | | | | 12.5 mg/kg | | | | | 25.0 mg/kg | | | | |
| Organ | Tissue | Change | 1 | 2 | 3 | 4 | 5 | 11 | 12 | 13 | 14 | 15 | 21 | 22 | 23 | 24 | 25 |
| Heart | Epicardium | | − | − | − | − | − | − | − | − | − | − | − | − | − | − | − |
| | Myocardium | Focal collapse | − | + | − | − | − | + | − | − | + | − | − | − | − | − | − |
| | Endocardium | | − | − | − | − | − | − | − | − | − | − | − | − | − | − | − |
| Spleen | | Atrophy | − | − | − | − | − | − | − | − | − | − | − | − | − | − | − |
| | | Congestion | − | − | − | − | − | − | − | − | − | − | − | − | − | − | + |
| | | Haemosiderosis | + | + | + | + | + | + | + | + | + | + | + | + | + | + | + |
| Lymph node | | | − | − | − | − | − | − | − | − | − | − | − | − | − | − | − |
| Bone marrow | | Hypoplasia | − | − | − | − | − | − | − | − | − | − | − | − | − | − | − |
| Lung | Alveolus | Pneumonia | − | + | − | − | − | − | + | − | − | − | − | − | + | + | − |
| | Alveolar wall | Pneumonia | − | − | − | − | − | − | − | − | − | − | − | − | − | − | − |
| | | Congestion | − | − | − | − | − | − | − | − | − | − | − | − | − | − | − |
| | Bronchus | Bronchitis | − | − | − | − | − | − | − | − | + | − | − | − | − | − | − |
| Salivary | Serous gl. | Atrophy | − | − | − | − | − | − | − | − | − | − | ++ | ++ | ++ | ++ | ++ |
| | Mucous gl. | | − | − | − | − | − | − | − | − | − | − | − | − | − | − | − |
| Stomach | | | − | − | − | − | − | − | − | − | − | − | − | − | − | − | − |
| Intestine | | | − | − | − | − | | | | | | | | | | | |
| Intestine | − | − | − | − | − | − | | | | | | | | | | | |
| Liver | Liver cell | Degeneration | − | − | − | − | − | − | − | − | − | − | − | − | − | − | − |
| | Liver cell cord | Cell inf. | − | + | − | − | + | − | − | + | − | − | − | − | − | − | + |
| | | Congestion | − | − | − | − | − | − | − | − | − | − | − | − | − | − | − |

TABLE 11-A-continued

Histopathological Findings of Rats Treated Orally with MR

| Organ | Tissue | Change | Control 1 | 2 | 3 | 4 | 5 | 12.5 mg/kg 11 | 12 | 13 | 14 | 15 | 25.0 mg/kg 21 | 22 | 23 | 24 | 25 |
|---|---|---|---|---|---|---|---|---|---|---|---|---|---|---|---|---|---|
|  | Kupffer cell | Swelling | − | + | − | − | + | − | − | + | + | − | + | − | + | − | + |
|  | Glisson's capsule | Cell inf. | − | + | + | − | + | − | + | + | + | + | + | − | − | + | + |
| Pancreas |  |  | − | − | − | − | − | − | − | − | − | − | − | − | − | − | − |
| Kidney |  |  | − | − | − | − | − | − | − | − | − | − | − | − | − | − | − |
| Urine bladder |  |  | − | − | − | − | − | − | − | − | − | − | − | − | − | − | − |
| Testis |  |  | − | − | − | − | − | − | − | − | − | − | − | − | − | − | − |
| Prostate |  |  | − | − | − | − | − | − | − | − | − | − | − | − | − | − | − |
| Hypophysis |  |  | − | − | − | − | − | − | − | − | − | − | − | − | − | − | / |
| Thymus | Atrophy |  | − | − | − | − | − | − | − | − | − | − | − | − | − | − | − |
| Thyroid |  |  | − | − | − | − | − | − | − | − | − | − | − | − | − | − | − |
| Adrenal | Hypertrophy |  | − | − | − | − | − | − | − | − | − | − | − | − | − | + | − |
| Central nerve |  |  | − | − | − | − | − | − | − | − | − | − | − | − | − | − | − |

/ : No examination
− : No pathological change
+ : Slight change
++ : Moderate change

TABLE 11-B

Histopathological Findings of Rats Treated Orally with MR

| Organ | Tissue | Change | 50.0 mg/kg 31 | 32 | 33 | 34 | 35 | 100.0 mg/kg 41 | 42 | 43 | 44 | 45 | 200.0 mg/kg 51* | 52* | 53* | 54* | 55* |
|---|---|---|---|---|---|---|---|---|---|---|---|---|---|---|---|---|---|
| Heart | Epicardium |  | − | − | − | − | − | − | − | − | − | − | − | − | − | − | − |
|  | Myocardium | Focal collaspe | − | − | + | − | − | − | − | − | + | − | − | − | − | + | − |
|  | Endocardium |  | − | − | − | − | − | − | − | − | − | − | − | − | − | − | − |
| Spleen |  | Atrophy | − | − | − | − | − | − | − | − | − | − | − | − | − | − | − |
|  |  | Congestion | − | − | − | − | − | − | ++ | + | + | + | ++ | ++ | ++ | + | + |
|  |  | Haemosiderosis | + | + | + | + | + | + | + | + | + | + | + | + | + | + | + |
| Lymph node |  |  | − | − | − | − | − | − | − | − | − | − | / | / | / | / | / |
| Bone marrow |  | Hypoplasia | − | − | − | − | − | − | + | − | + | + | ++ | / | / | ++ | / |
| Lung | Alveolus | Pneumonia | − | − | + | + | − | + | + | − | − | − | − | − | − | − | − |
|  | Alveolar wall | Pneumonia | − | − | − | − | − | − | − | − | − | − | ++ | ++ | ++ | + | + |
|  |  | Congestion | − | − | − | − | − | − | − | − | − | − | + | ++ | ++ | ++ | +++ |
|  | Bronchus | Bronchitis | − | − | − | − | − | − | − | − | − | − | − | − | − | − | − |
| Salivary | Serous gl. | Atrophy | ++ | ++ | ++ | ++ | ++ | + | + | − | + | − | − | − | − | − | − |
|  | Mucous gl. |  | − | − | − | − | − | − | − | − | − | − | − | − | − | − | − |
| Stomach |  |  | − | − | − | − | − | − | − | − | − | − | − | − | − | − | − |
| Intestine |  |  | − | − | − | − | − | − | − | − | − | − | − | − | − | − | − |
| Liver | Liver cell | Degeneration | − | − | − | − | − | − | − | − | − | − | +++ | ++ | ++ | ++ | ++ |
|  | Liver cell cord | Cell inf. | − | − | − | − | − | − | + | − | − | − | + | − | + | − | − |
|  |  | Congestion | − | − | − | − | − | + | − | − | − | ++ | ++ | ++ | ++ | ++ | +++ |
|  | Kupffer cell | Swelling | − | ++ | − | − | − | − | + | + | − | − | ++ | + | + | + | + |
|  | Glisson's capsule | Cell inf. | − | + | − | − | − | − | + | + | − | − | − | − | − | + | − |
| Pancreas |  |  | − | − | − | − | − | − | − | − | − | − | − | − | − | − | − |
| Kidney |  |  | − | − | − | − | − | − | − | − | − | − | − | − | − | − | − |
| Urine bladder |  |  | − | − | − | − | − | − | − | − | − | − | − | − | − | − | − |
| Testis |  |  | − | − | − | − | − | − | − | − | − | − | − | − | − | − | − |
| Prostate |  |  | − | − | − | − | − | − | − | − | − | − | − | − | − | − | / |
| Hypophysis |  |  | − | − | − | − | − | − | − | − | − | − | − | − | − | − | − |
| Thymus | Atrophy |  | − | − | − | − | − | − | − | − | − | − | +++ | / | +++ | / | / |
| Thyroid |  |  | − | − | − | − | − | − | − | − | − | − | / | − | − | − | / |
| Adrenal |  | Hypertrophy | + | + | ++ | + | + | + | + | + | + | + | − | − | − | + | − |
| Central nerve |  |  | − | − | − | − | − | − | − | − | − | − | − | − | − | − | − |

/: No examination
−: No pathological change
+: Slight change
++: Moderate change
+++: Marked change
*: Dead case From the above-described sub-acute toxicity test, ineffective dose and lethal dose of MR to rats are defined as 12.5 mg/kg and 200 mg/kg respectively. On the other hand, ineffective dose and lethal dose of RCN were found, from the sub-acute toxicity test which we conducted, to be 6 mg/kg and 36 mg/kg respectively.

In view of the fact that an ineffective dose of MR is nearly equal to that of RCN or higher, and that a lethal dose of MR is about 3 to 5 times that of RCN, MR is considered to be a safer substance than RCN.

As side effects, there were observed blepharoptosis, leukopenia, increase of urine volume, atrophy of hematopoietic organs, cortial hypertrophy of adrenal and degeneration of liver cells (in dead rats) only at the higher doses. Out of the side effects, pathological changes in adrenal and liver were not reported in connection with RCN. However, the pathological change of adrenal is a reversible hypertrophy of cortex causes by hyperfunction, and the morbid change of liver was formed only in dead animals of the highest dose. Also, taking into consideration that there was found no pathological change by histopathological examination of kidney, the increase in urine volume at higher doses seems to be a diuretic effect, which is a desirable property in a hypertensive remedy. There was observed no pathological change of stomach mucous which often occurs when RCN is used.

Based on long clinical use of RSP and RCN, it can be said that MR, the metabolite thereof, has been actually, though without any recognition, used clinically, and therefore, it is concluded that MR is a hypertensive remedy of very high safety.

EXAMPLE 5

This example illustrates the experiment conducted for the purpose of detailed analysis of the medical effect and the toxicity of the metabolism of MR.

Animals used:

Male, adult cross-bred dogs weighing about 10 kg; male rabbits weighing about 3 kg; and male S.D.-strain rats weighing about 150 g. In case of oral administration, the animals were not permitted to eat for 24 hours, except for the experiment of biotransformation.

Experimental Method:

MR was dispersed in 0.2% carboxymethyl cellulose solution and administered to the animals at a dose of 10 mg/kg-weight for oral administration, or 1 ml/kg-weight for veous injection.

Blood was drawn from branchial vein of dogs, vein of ear of rabbits and carotic artery of rats after slaughter. Urine was collected with urine bladder catheter for rabbits and metabolic cages for rats. Gathering bile was performed with biliary duct cannulation without anesthesia. Quantitative analysis of MR in biological fluids were made in accordance with fluorescencemetry established by Glazco et al.

(a) Change of MR-Content in Blood

Figure 13:
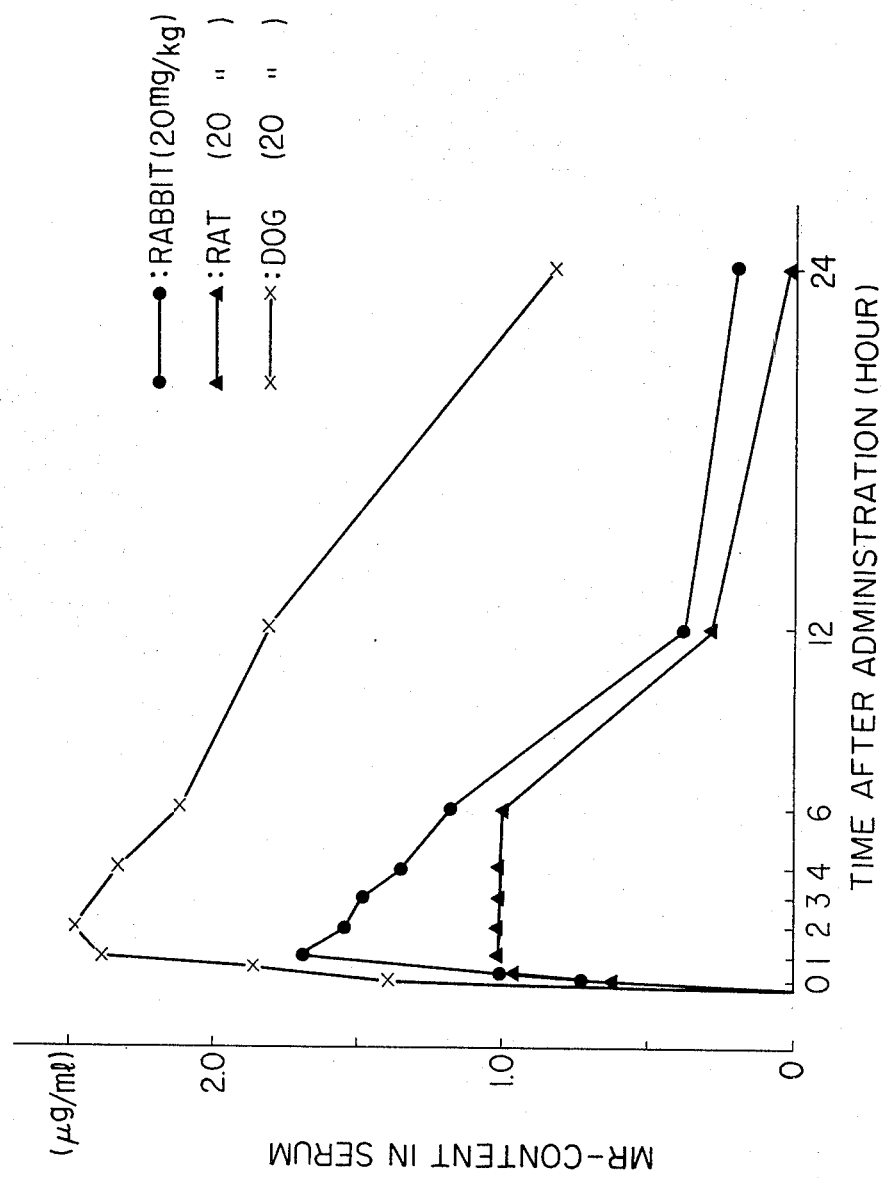
FIG. 13 shows changes of MR content in serum after oral administration.
Figure 14:
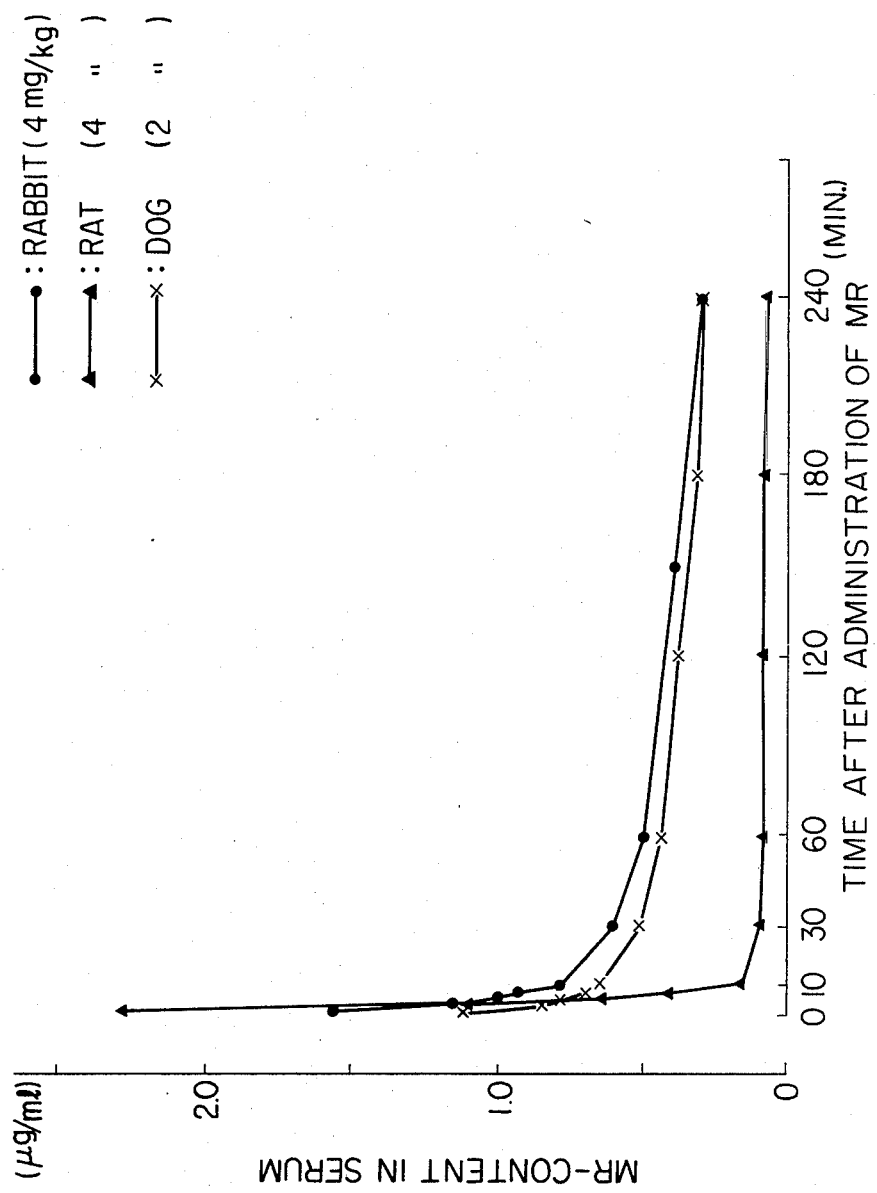
FIG. 14 shows changes of MR content in serum after administration by venous injection.

FIG. 13 and FIG. 14 show change of unchanged in serum material of dogs, rabbits and rats to which MR was administered orally or by venous injection.

The pattern of the serum levels showed high corralation with the pattern of blood pressure decrease, and hence, measurement of the serum level is likely to be used as a parameter of the medical effect, and in clinical application this is expected to useful for planning the administration of MR.

Figure 15:
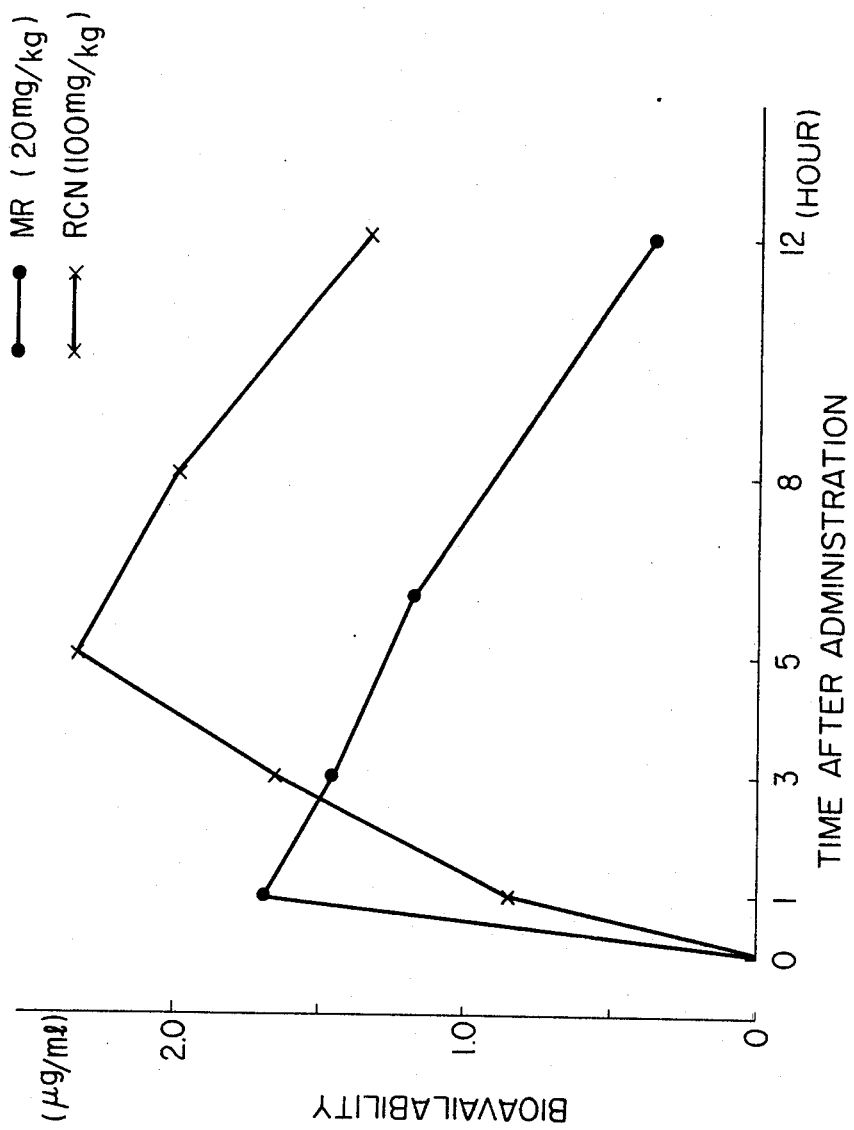
FIG. 15 shows comparison of bioavailabilities of MR and RCN when orally administered to rabbits.

FIG. 15 shows bioavailability of orally administered MR in comparison with that of RCN.

FIGS. 13 and 14 indicate that, in spite of the fact that MR is a metabolite of RSP and RCN, MR is more readily absorbed from digestive tracts, and that the serum level, reaches a maximum level 1 to 2 hours after the administration, and further, that the period of residence in bodies is rather longer.

In regard to FIG. 15, the area under the curve of MR content in serum was calculated on the following basis:

| Medicine | Bioavailability Area under the Curve of MR Content in Serum (20 mg/kg) | Ratio |
| --- | --- | --- |
| MR | 63.6 | 1 |
| RCN | 20.2* | 0.32 |

*The value based on converting the data in Figure 15 to 20 mg/kg basis.

(b) Excretion into Urine and Bile

Figure 16:
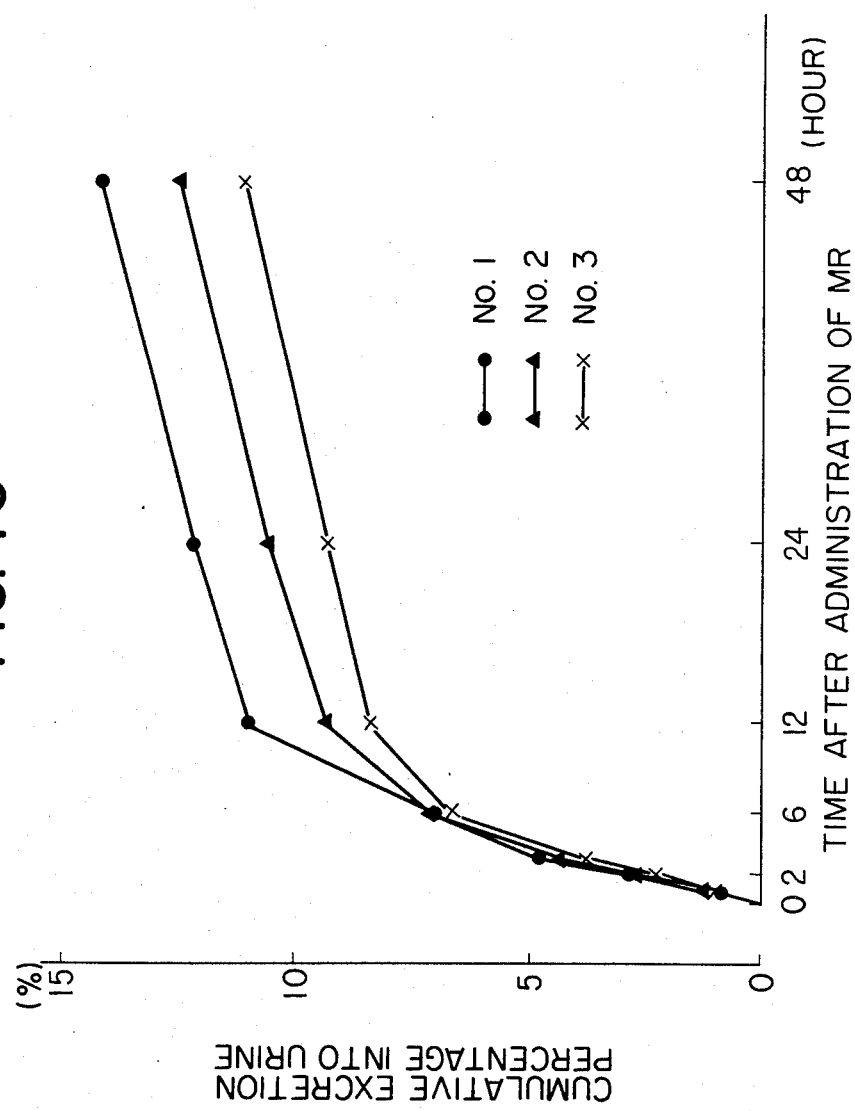
FIG. 16 shows cumulative excretion percentage of MR into urine when orally administered or rabbits.

FIG. 16 shows change by time of excretion percentage of MR into urine in case of oral administration to rabbits. From the figure it is recognized that 10 to 15% of the administered MR is discharged into urine within 48 hours after administration, and that the rate of discharge is the highest between 1 to 4 hours after shows a high correlation with the above-mentioned change in MR content in blood after oral administration.

Figure 17:
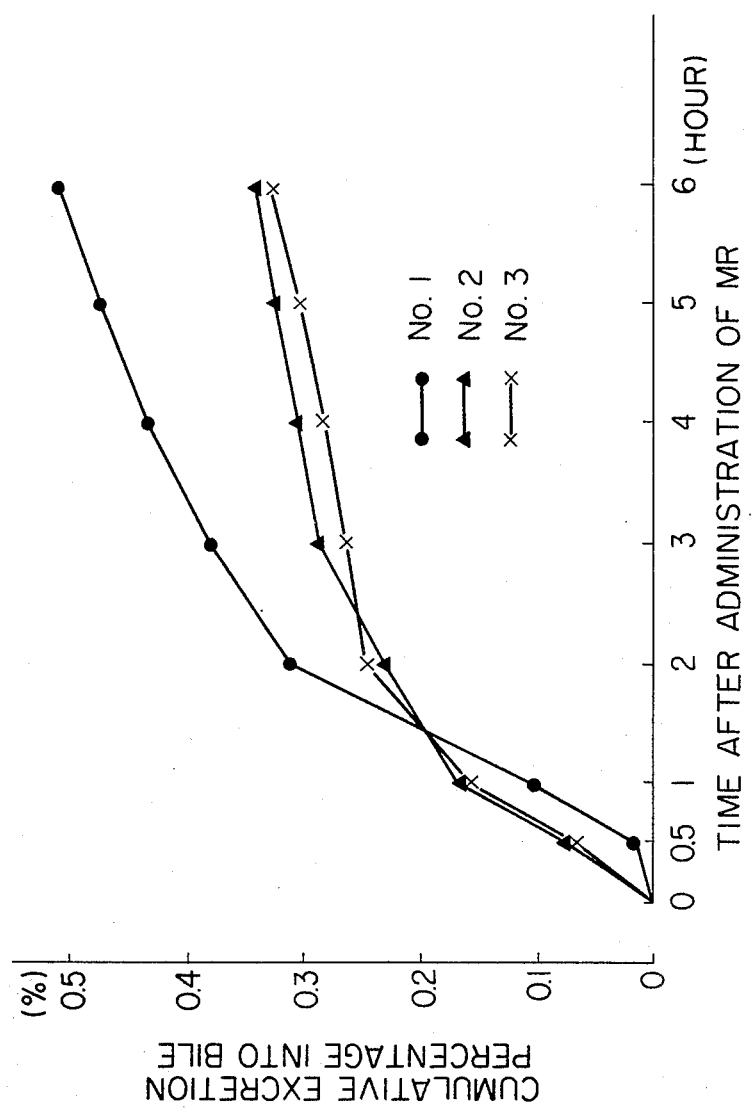
FIG. 17 shows cumulative excretion percentage of MR into bile when administered by venous injection to rabbits.

FIG. 17 shows change by time of excretion percentage of MR into bile in case of venous injection to rabbits. From the Figure it is recognized that an amount as small as 0.3 to 0.5% of the administered MR is discharged into bile within 6 hours after administration. As a conclusion, the main route of excretion of MR is discharge into urine.

(c) Biotransformation 100 mg/kg of MR was administered to 10 rats every day over 18 days to collect urine.

Figure 18:
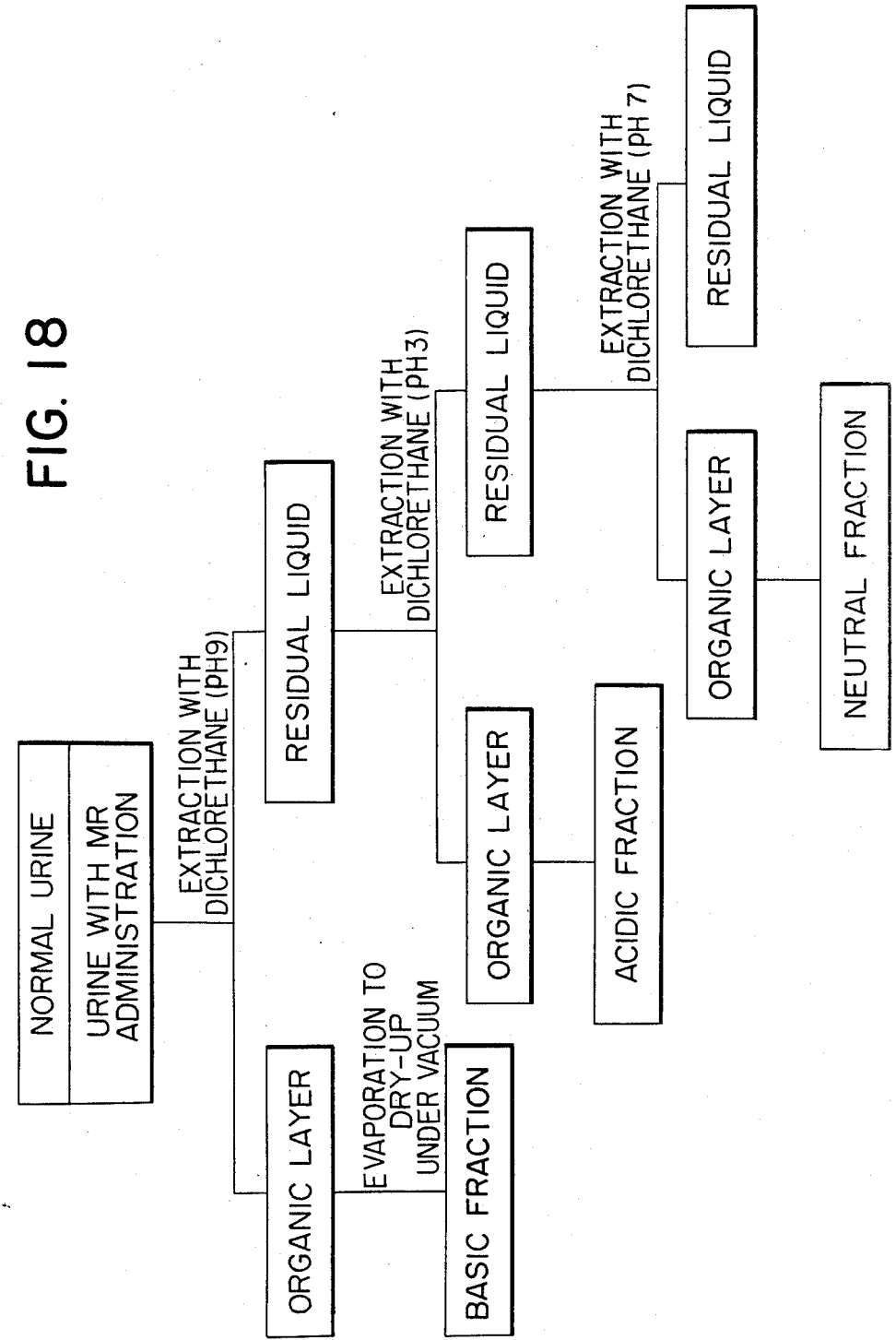
FIG. 18 shows a process for extraction of substances discharged into urine.

Extraction was carried out in accordance with the procedure given in FIG. 18 to obtain, as dichloroethane extract, 0.56 g of basic fraction. The survey on discharged substances in the fractions through thin layer chromatography disclosed that there are two kinds of excreted substances: M-I and M-II. M-I and M-II, through thin layer chromatography, were separated from ordinary components of urine to give about 220 mg and 5 mg respectively.

Structural approach of M-I and M-II by NMR, MS, IR and UV proved that M-I is identical with MR, and that M-II is a demethylated product of MR at methoxy group of "A" ring.

As a result of the above study through the survey of MR-originated substances having biological activities, it is concluded that MR is hardly metabolized when orally administered and mainly the unchanged MR exhibits the effects.

In FIG. 16, the excretion percentage into urine is defined as a percentage of the amount discharged into urine to the amount administered; and in FIG. 17, the excretion percentage into bile is defined as a percentage of the amount discharged into bile to the amount administered.

We claim:

1. A treating method of hypertension in humans comprising orally administering an effective amount of methylreserpate.

* * * * *